(12) United States Patent
Park et al.

(10) Patent No.: US 7,838,690 B2
(45) Date of Patent: Nov. 23, 2010

(54) METHOD FOR PREPARING CRYSTALLINE 3-0-ALKYL-ASCORBIC ACID

(75) Inventors: Sung-Ryoung Park, Kyeongki-do (KR); Geon-Min Lee, Kyeongki-do (KR)

(73) Assignee: Cosmol Co. Ltd, Kyeongki-do (KR)

( * ) Notice: Subject to any disclaimer, the term of this patent is extended or adjusted under 35 U.S.C. 154(b) by 69 days.

(21) Appl. No.: 12/444,821

(22) PCT Filed: Dec. 7, 2006

(86) PCT No.: PCT/KR2006/005274

§ 371 (c)(1),
(2), (4) Date: Apr. 8, 2009

(87) PCT Pub. No.: WO2008/044809

PCT Pub. Date: Apr. 17, 2008

(65) Prior Publication Data

US 2010/0048919 A1    Feb. 25, 2010

(30) Foreign Application Priority Data

Oct. 12, 2006    (KR) .................. 10-2006-0099554

(51) Int. Cl.
*C07D 307/62* (2006.01)
(52) U.S. Cl. ..................................... 549/315
(58) Field of Classification Search .................. 549/315
See application file for complete search history.

(56) References Cited

U.S. PATENT DOCUMENTS 4,552,888 A    11/1985   Koppel et al.

FOREIGN PATENT DOCUMENTS

| JP | 58-057373 A | 4/1983 |
| KR | 1020010070672 A | 7/2001 |
| KR | 1020040088312 A | 10/2004 |
| KR | 100600435 B1 | 7/2006 |

OTHER PUBLICATIONS

Kato et al.; "Studies on Scavengers of Active Oxygen Species. 1. Synthesis and Biological Activity of 2-O-Alkylascorbic Acids"; J. Med. Chem.; 1988; pp. 793-798; vol. 31.
Jackson et al.; "The C- and O-Benzylation of L-Ascorbic Acid"; Canadian Journal of Chemistry; 1965; pp. 450-457; vol. 43.

*Primary Examiner*—D. Margaret Seaman
*Assistant Examiner*—Nizal S Chandrakumar
(74) *Attorney, Agent, or Firm*—The Webb Law Firm

(57) ABSTRACT

The present invention relates to a method for preparing 3-O-substituted ascorbic acid derivatives represented by formula 1, in which 5,6-O-isopropylidene ascorbic acid is reacted with a halide in an organic solvent in the presence of the anion exchange resin absorbed with multi-iodine anions and then deprotected. The method of the present invention has an advantage of providing a target compound with high purity and high yield by finishing the reaction within a short period of time at room temperature.

6 Claims, No Drawings

METHOD FOR PREPARING CRYSTALLINE 3-0-ALKYL-ASCORBIC ACID

TECHNICAL FIELD

The present invention relates to a method for preparing crystalline 3-O-alkyl-ascorbic acid, the 3-O-substituted ascorbic acid, particularly by reacting 5,6-O-isopropylidene ascorbic acid with a halide in an organic solvent in the presence of the anion exchange resin absorbed with multi-iodine anions, leading to deprotection.

BACKGROUND ART

L-ascorbic acid is a bioactive material having a strong anti-oxidative activity, which has been used as a medicine for treating scurvy and at the same time applied to cosmetics owing to its wide physiological activities including inhibiting the accumulation of melanic pigments, known as a cause of chloasma or freckles. In addition, owing to its effects of increasing collagen bio-synthesis and stimulating fibroblast growth, L-ascorbic acid has also been used to prevent browning of food, preserve incense and maintain freshness.

However, the ascorbic acid is easily oxidized by heat, light and oxygen in the air to lose its activity and is insoluble in oil, so that it has been limited in use.

In particular, the ascorbic acid is more easily oxidized in water phase. Thus, when it is included in a medicinal compound, cosmetics and food, its titer is decreased and discoloration is observed during the production processes or long term storage.

To improve stability of the ascorbic acid, numbers of ascorbic acid derivatives have been developed, and particularly studies on 3-substituted ascorbic acids have been focused on L-ascorbic acids with the substitution of the $3^{rd}$ hydroxyl group (OH) with lower alkyl, lower alkylcarbonyl, or lower alkenyl.

The preparation of ascorbic acid derivatives by alkylation of an ascorbic acid is described in US Patent No. 4552888, Can. J. Chem., 43, 450 (1965) and J. Med. Chem., 31, 793 (1988). According to these descriptions, ascorbic acid is reacted with sodium methoxide (NaOMe) in such a solvent as dimethylsulfoxide (DMSO) or dimethylformamide (DMF) to give ascorbic acid sodium salt, which would be reacted with alkylhalide. However, according to the method, the substitution of the $3^{rd}$ hydroxyl group of the ascorbic acid with alkyl is limited and the generation of byproducts is another problem.

The limitation of DMSO or DMF in use is further attributed to its high boiling point along with that the 3-substituted ascorbic acid derivative is highly soluble in a polar solvent, making purification very difficult (column chromatography has to be necessarily used in most cases) and providing low yield.

As an effort to overcome the above problem of the conventional method, Japanese Laid-Open Patent Publication No. S 58-57373 describes that the $5^{th}$ and the $6^{th}$ hydroxyl group (OH) of L-ascorbic acid are protected by isopropylidene group and 5,6-O-isopropylidene ascorbic acid, the precursor thereof, is synthesized (step 1). In step 2, alkylhalide is reacted with 5,6-O-isopropylidene ascorbic acid to give 3-O-alkyl-5,6-O-isopropylidene ascorbic acid. In step 3, to recover the original hydroxyl groups at the $5^{th}$ and the $6^{th}$ position of 3-O-alkyl-5,6-O-isopropylidene ascorbic acid, the generated protecting group is broken by hydrogenation (hydrolysis), resulting in 3-O-alkyl-ascorbic acid. However, in step 3, the use of a strong polar solvent results in the decrease of yield.

Korean Patent Publication No. 2001-70672 and No. 2004-88312 describe a method for preparing 3-O-substituted ascorbic acid comprising the following steps.

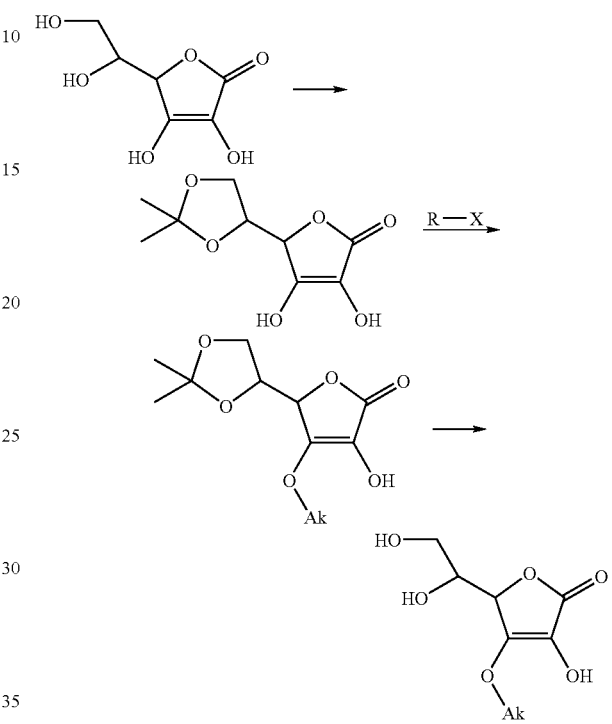

However, the low yield of alkylation of 3-hydroxyl group and sub-reactions caused by the overuse of alkylhalide were pointed out as disadvantages of the method with the request of the elaborate purification of produced 3-O-alkyl-5,6-O-isopropylidene ascorbic acid.

DISCLOSURE

Technical Problem

It is an object of the present invention, to solve the problems of the conventional methods for preparing ascorbic acids, to provide a method for preparing 3-O-substituted ascorbic acid with high yield.

Technical Solution

The present invention provides a method for preparing 3-O-substituted ascorbic acid represented by the following formula 1, which is characterized by the steps of a) preparing 3-O-substituted-5,6-O-isopropylidene ascorbic acid represented by the following formula 4 by reacting 5,6-O-isopropylidene ascorbic acid represented by the following formula 2 with a halide represented by the following formula 3 in an organic solvent in the presence of the anion exchange resin absorbed with multi-iodine anions; and b) deprotecting the 3-O-substituted-5,6-O-isopropylidene ascorbic acid represented by the following formula 4.

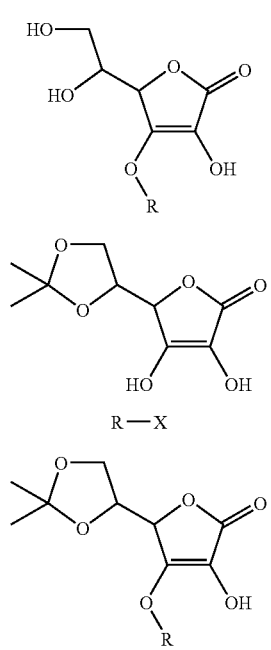

[Formula 1]

[Formula 2]

[Formula 3]

[Formula 4]

[In formula 1, formula 3 and formula 4, R is C1~C7 alkyl or alkenyl and X is halogen atom.]

The preferable content of the anion exchange resin absorbed with multi-iodine anions is 0.5~5 weight % of 5,6-O-isopropylidene ascorbic acid. The acceptable reaction temperature is room temperature ~70° C. But, the reaction is completed at room temperature within an hour so the preferable reaction temperature to avoid sub-reactions is room temperature.

Upon completion of the reaction, the anion exchange resin absorbed with multi-iodine anions is eliminated by using a filter from the reactant. Alkylhalide is then eliminated by vacuum-distillation and then re-crystallization is induced in a relevant solvent to give 3-O-substituted-5,6-O-isopropylidene ascorbic acid with high purity. The 3-O-substituted-5,6-O-isopropylidene ascorbic acid is deprotected by the conventional method to give 3-O-substituted ascorbic acid.

The anion exchange resin absorbed with multi-iodine anions of the present invention can be prepared by the method described in Korean Patent No. 600435, in which iodide alkaline and iodine ($I_2$) are mixed at the molar ratio of 1:1~5 to prepare iodine anion solution and the anion exchange resin containing polymer particles are immersed therein.

The multi-iodine anion solution is preferably prepared by mixing one or more iodide salts ($I^-$), selected from a group consisting of potassium iodide and sodium iodide, and iodine ($I_2$) at the molar ratio of 1:1~5 and more preferably 1:1~3. For example, 0.6 kg of potassium iodide (KI), as an iodide salt, and 0.9 kg of iodine ($I_2$) are mixed in 300 mL of water, resulting in triiodide ($I_3^-$).

According to the preparing method of the present invention, alkylation is accelerated by the multi-iodine anions ($I_3^-$, $I_5^-$, $I_7^-$ etc.) adsorbed on the anion exchange resin, so that the reaction for substitution is induced with high yield within a short period of time even at room temperature to give a target subject.

The anion exchange resin of the present invention is round shaped or granular type and is prepared by the processes of adding methylene chloride radical to the copolymer of divinylbenzene and polystyrene; and reacting the mixture with amine. At this time, porosity is regulated by the amount of divinylbenzene. Amberite series (IRA-410, IRA-411, IRA-400, IRA-402, IRA900, IRA-938, IRA-910, IRA-900C, IRA-93, IRA-94), Dowex series (2×8(SAR), 1×8(SBR), 21K (SBRP), MSA-1, 21K(SBR-P), KWA-1) and Diaion series (SA20A, SA10A, SA12A, SA11A, PA312, PA418, PA312L, WA30) are the examples of the anion exchange resin.

The organic solvent used in step a) can be any solvent as long as it is aprotic, which is exemplified preferably by dimethyl sulfoxide, dimethylformamide, methylpyrrolidone, dimethylacetamide and acetonitrile.

3-O-substituted ascorbic acid is prepared by the conventional deprotection from the 3-O-substituted-5,6-O-isopropylidene ascorbic acid obtained in step a). And the deprotection is induced in hydrochloric acid solution in the presence of methanol or ethanol. Herein, perfluorosulfonic acid resin composed of the copolymer of tetrafluoroethylene and sulfonyl chloride vinyl ether presented by Nafion H (Dupon) is preferably used. Nafion H which maintains heat-resistance at over 200° C. is recovered from the reaction mixture by post-reaction filtering process and used as it is or after being regenerated.

The preferable content of Nafion H for the deprotection is 0.5~20 weight % of 3-O-substituted-5,6-O-isopropylidene ascorbic acid. At this time, the mixed solvent of water and ethanol (1:10~20) is preferred and the preferable reaction temperature ranges from room temperature to 70° C.

It is an advantage of the deprotection using Nafion H that the reactant 3-O-substituted ascorbic acid has high purity, compared with when the deprotection is performed in hydrochloric acid solution.

BEST MODE

Hereinafter, the embodiments of the present invention will be described in detail with reference to accompanying drawings.

EXAMPLES 0.6 kg of potassium iodide and 1.8 kg of iodine ($I_2$) were dissolved in 300 ml of water to prepare iodide ($I_5^-$) solution. 20 g of the anion exchange resin (Amberite, IRA-402) was immersed in the prepared iodide solution for 24 hours and the adhered iodo compound was eliminated by dipping in fresh water for 24 hours.

The mixture was filtered and washed with distilled water until the mixture became neutral. The above process was repeated 4 times and then the product was dried at 80~90° C. under the reduced pressure (10 mmHg) to give Nafion H.

Example 1

Synthesis of 5,6-O-isopropylidene Ascorbic Acid

To the mixed solvent composed of 100 mL of dimethylsulfoxide and 40 ml of acetone were added 17.6 g of L-ascorbic acid, 15.6 g of 1,2-dimethoxypropane and 1.2 g of p-tolusulfonic acid, followed by stirring for 5 hours at 50° C. The produced reaction mixture was vacuum-distilled at 20° C. to eliminate the remaining acetone and non-reacted 1,2-dimethoxypropane to give 20.5 g of the target compound (yield: 95%).

Example 2

Synthesis of L-3-O-ethyl-isopropylidene Ascorbic Acid

To 100 mL of DMF were added 20.5 g (0.095 mol) of 5,6-O-isopropylidene ascorbic acid prepared in Example 1 and 1.0 g of the anion exchange resin absorbed with multi-iodine anions, to which 12.3 g (0.11 mol) of ethylbromide was slowly loaded at room temperature with stirring. Upon completion of the loading, stirring at room temperature was continued for 3 hours and then the anion exchange resin absorbed with multi-iodine anions was filtered from the reaction mixture. DMF and ethylbromide were eliminated by vacuum-distillation. Then, 180 ml of water and ethylacetate (120 ml×2) were added to separate an organic layer, which was then collected. The organic layer was concentrated under the reduced pressure and the residue was re-crystallized in ethylacetate/hexane (1:1) to give 22.0 g of 3-O-ethyl-isopropylidene ascorbic acid (yield: 95%).

mp: 105~106° C. $^1$H NMR (MeOH-d$_4$) ppm, δ 1.28 (6H,S) 1.34 (3H, t) 4.12 (3H, m) 4.51 (2H, q) 4.65 (1H, d, 3 Hz)

Example 3

Preparation of L-3-O-ethyl-ascorbic Acid 12.4 g of the 3-O-ethyl-isopropylidene ascorbic acid obtained in Example 1 was dissolved in 100 ml of distilled water, to which 10 ml of 2N hydrochloric acid solution was added. The mixture was reacted at 60° C. for 2 hours and concentrated under reduced pressure to give an adhesive liquid product. Ethanol was added to the prepared liquid product, which was then concentrated to give crude crystalline 3-ethyl-ascorbic acid. The crude crystalline 3-ethyl-ascorbic acid was re-crystallized in ethylacetate/ethanol (8:2) to give 8.6 g of white crystalline 3-O-ethyl-ascorbic acid (yield: 84.3%).

mp: 113~114° C. $^1$H NMR (MeOH-d$_4$) ppm, δ 1.36 (3H, t) 3.58~3.67 (2H, m) 3.77~3.85 (1H, m) 4.54 (2H, q) 4.75 (1H, d, 1.3 Hz)

Example 4

Preparation of L-3-O-ethyl-ascorbic Acid 12.4 g of the 3-O-ethyl-isopropylidene ascorbic acid prepared in Example 1 was dissolved in the mixed solvent of distilled water (10 ml)/ethanol (90 ml) together with 1.1 g of Nafion H, followed by stirring at 60° C. for 2 hours. Nafion H was eliminated by filtering and the mixture was concentrated into crude crystalline 3-ethyl-ascorbic acid. The crude crystalline 3-ethyl-ascorbic acid was re-crystallized in ethylacetate/ethanol (8:2) to give 7.6 g of white crystalline 3-O-ethyl-ascorbic acid.

mp: 113~114° C. $^1$H NMR (MeOH-d$_4$) ppm, δ1.36 (3H, t) 3.58~3.67 (2H, m) 3.77~3.85 (1H, m) 4.54 (2H, q) 4.75 (1H, d, 1.3 Hz)

INDUSTRIAL APPLICABILITY

The preparation method of the present invention has an advantage of providing a target compound with high yield and high purity by reaction at room temperature within a short period of time, which is economical, efficient mass-production method.

The invention claimed is:

1. A method for preparing 3-O-substituted ascorbic acid represented by the following formula 1, comprising the following steps:
   a) Preparing 3-O-substituted-5,6-O-isopropylidene ascorbic acid represented by the following formula 4 by reacting 5,6-O-isopropylidene ascorbic acid represented by the following formula 2 with a halide represented by the following formula 3 in an organic solvent in the presence of the anion exchange resin absorbed with multi-iodine anions; and
   b) Deprotecting the 3-O-substituted-5,6-O-isopropylidene ascorbic acid represented by the following formula 4;

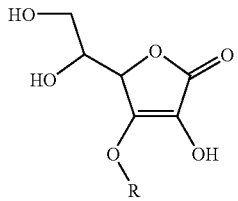

[Formula 1]

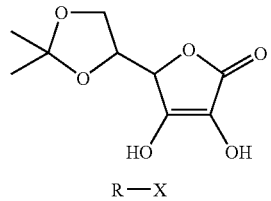

[Formula 2]

R—X [Formula 3]

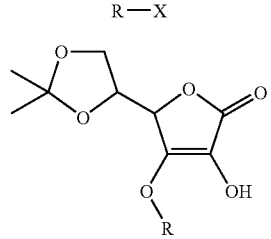

[Formula 4]

[In formula 1, formula 3 and formula 4, R is C1~C7 alkyl or alkenyl and X is halogen atom].

2. The method for preparing 3-O-substituted ascorbic acid according to claim 1, wherein the anion exchange resin absorbed with multi-iodine anions is prepared by immersing the anion exchange resin containing polymer in the multi-iodine anion solution composed of iodide alkaline and iodine (I$_2$) at the molar ratio of 1:1~5.

3. The method for preparing 3-O-substituted ascorbic acid according to claim 1, wherein the content of the anion exchange resin absorbed with multi-iodine anions is 0.5~5 weight % of 3-O-substituted-5,6-O-isopropylidene ascorbic acid.

4. The method for preparing 3-O-substituted ascorbic acid according to claim 1, wherein the reaction temperature of step a) ranges from room temperature to 70° C.

5. The method for preparing 3-O-substituted ascorbic acid according to claim 1, wherein the organic solvent of step a) is one or more compounds selected from a group consisting of dimethyl sulfoxide, dimethylformamide, methylpyrrolidone, dimethylacetamide, and acetonitrile.

6. The method for preparing 3-O-substituted ascorbic acid according to claim 1, wherein the deprotection of step b) is performed in the mixed solvent of ethanol and water in the presence of the perfluorosulfonic acid resin.

* * * * *